United States Patent [19]

Nguyen et al.

[11] Patent Number: 5,873,981
[45] Date of Patent: Feb. 23, 1999

[54] RECOVERY OF ANHYDROUS ACIDS

[75] Inventors: Son T. Nguyen, Lake Jackson; Louis L. Walker, Clute; Katherine S. Clement, Lake Jackson, all of Tex.

[73] Assignee: The Dow Chemical Company, Midland, Mich.

[21] Appl. No.: 773,116

[22] Filed: Dec. 26, 1996

[51] Int. Cl.$^6$ .............. B01D 1/22; B01D 3/36; C07C 69/74
[52] U.S. Cl. .............. 203/15; 203/65; 203/89; 159/49; 159/DIG. 19; 562/124
[58] Field of Search .............. 203/15, 1, 3, 65, 203/89; 159/DIG. 19, DIG. 20, 49, DIG. 10; 562/124; 568/727, 745

[56] References Cited

U.S. PATENT DOCUMENTS

| | | | |
|---|---|---|---|
| 2,124,729 | 7/1938 | Castner et al. | 23/169 |
| 2,711,388 | 6/1955 | Mottern et al. | 202/53 |
| 4,450,047 | 5/1984 | Malzahn | 203/15 |
| 4,938,846 | 7/1990 | Cornstock et al. | 203/15 |
| 5,258,554 | 11/1993 | Langer et al. | 568/745 |
| 5,475,155 | 12/1995 | Hefner, Jr. et al. | 568/727 |

FOREIGN PATENT DOCUMENTS

| | | |
|---|---|---|
| 2042774 | 3/1971 | Germany . |
| 264543 | 11/1988 | Japan . |
| 305546 | 10/1992 | Japan . |
| 1282828 | 7/1972 | United Kingdom . |
| 1344864 | 1/1974 | United Kingdom . |

*Primary Examiner*—Virginia Manoharan

[57] ABSTRACT

A is a process for removing water from an alkanesulfonic acid such as methanesulfonic acid or ethanesulfonic acid by mixing an azeotropic excess of a phenolic compound with water and the alkanesulfonic acid, then boiling off substantially all of the water, and leaving as a remnant substantially all the alkanesulfonic acid and some of the phenol. This process is particularly useful for recycling an alkanesulfonic acid for a reaction which requires the phenolic compound as one of the reagents. One such reaction is the alkanesulfonic acid catalyzed condensation reaction of a phenolic compound with an α-haloketone to form a chlorinated intermediate of a dihydroxy-α-alkylstilbene such as 4,4'-dihydroxy-α-alkylstilbene (DHAMS).

11 Claims, No Drawings

RECOVERY OF ANHYDROUS ACIDS

BACKGROUND OF THE INVENTION

This invention relates to a process for removing water from a non-volatile acid. More particularly, this invention relates to removing water from an alkanesulfonic acid.

Lower-alkanesulfonic acids, particularly methanesulfonic acid (MSA) and ethanesulfonic acid, have been found to be particularly useful reagents in the condensation reaction of phenol and chloroacetone to form 4,4'-dihydroxy-α-methylstilbene (DHAMS). Although MSA is more expensive than sulfuric acid, waste stream levels are substantially reduced when MSA is used; unlike sulfuric acid, the combination of phenol and MSA forms a homogeneous mixture below the temperature at which the condensation reaction is typically performed (about −15° C.), thereby substantially reducing the requirement for waste-generating ancillary solvents. In view of the comparatively high cost of MSA, it would be desirable to find an economical means of dehydrating and recycling this reagent.

Methods for recovering acids are well known in the art. For example, U.S. Pat. No. 2,124,729 by Castner et al. discloses a reduced pressure, falling film evaporative method of removing water from water-containing acids. U.S. Pat. No. 2,711,388 by Mottern et al. discloses a flash distillation method for removing water from aqueous acids such as sulfuric acid and MSA. More recently, U.S. Pat. No. 4,450,047 by Malzahn and U.S. Pat. No. 4,938,846 by Constock et al. disclose reduced pressure, falling film evaporative methods for removing water from lower-alkanesulfonic acids.

It would be desirable to remove water from non-volatile acids, particularly MSA, under less rigorous conditions than those disclosed in the processes of the prior art. It would further be desirable to provide a method for the recovery and reuse of MSA in a process for preparing DHAMS.

SUMMARY OF THE INVENTION

The present invention is a process for separating water from an alkanesulfonic acid comprising the steps of: a) forming a first mixture containing water, an azeotropic excess of a phenolic compound, and the alkanesulfonic acid; and b) boiling or evaporating off from the first mixture substantially all of the water and a portion of the phenolic compound to form a second mixture containing the alkanesulfonic acid, the phenolic compound, and a substantial absence of water.

In a second aspect, the present invention is a process for removing water from alkanesulfonic acid comprising the steps of: a) condensing a first phenolic compound with an α-haloketone in the presence of an alkanesulfonic acid to form a halogenated intermediate of a dihydroxy-α-alkylstilbene; b) quenching the condensation reaction with water to form a two-phase mixture, wherein one of the phases contains primarily water and the alkanesulfonic acid; c) isolating the phase that contains primarily water and the alkanesulfonic acid, and adding thereto an azeotropic excess of a second phenolic compound to form a mixture of water, the alkanesulfonic acid, and the second phenolic compound; and d) boiling or evaporating substantially all of the water and a portion of the second phenolic compound from the mixture of water, the alkanesulfonic acid, and the second phenolic compound to form a substantially water-free remnant that contains the alkanesulfonic acid and the second phenolic compound.

The process of the present invention provides a cleaner and more efficient means of separating water from an alkanesulfonic acid. Moreover, the process is particularly suitable for separations of water from alkanesulfonic acids where the acid and phenolic compound are used in a subsequent reaction.

DETAILED DESCRIPTION OF THE INVENTION

A dihydroxy-α-alkylstilbene can be prepared, for example, by the condensation of an α-haloketone with a first phenolic compound in the presence of an alkanesulfonic acid to form a halogenated intermediate which can then be dehydrohalogenated to form a dihydroxyα-alkylstilbene. Suitable first phenolic compounds are described in detail in Hefner, Jr. et al. in U.S. Pat. No. 5,475,155 (hereinafter "Hefner"), column 4, line 64 to column 5, line 28. Suitable α-haloketones include those disclosed by Hefner, column 5, line 65 to column 6, line 27; all of which disclosures are incorporated herein by reference. Phenol is the most preferred first phenolic compound; chloroacetone is the most preferred α-haloketone.

After a satisfactory amount of the halogenated intermediate is formed (as determined, for example, by monitoring the reaction by liquid chromatography), the alkanesulfonic acid is advantageously separated from the halogenated intermediate by first quenching the condensation reaction with cold water (about 0° C. to about 5° C.) and a cold, water-immiscible solvent such as methylene chloride to form a biphasic mixture, then separating the aqueous phase, which contains a substantial portion of the alkanesulfonic acid, from the phase that contains the chlorinated intermediate. The chlorinated intermediate phase is preferably washed a sufficient number of times with cold water to remove substantially all the acid therefrom so that the acid is present at a concentration of not more than about 10,000 ppm, preferably not more than about 5000 ppm, more preferably not more than about 1000 ppm, and most preferably not more than about 100 ppm.

The aqueous phase is preferably washed with a water-immiscible solvent such as methylene chloride to extract extractable organics therefrom. The aqueous layer is then advantageously heated, preferably under reduced pressure, to remove residual water-immiscible solvent. This heating step may also serve to precipitate any insoluble thermal byproduct, which can then be filtered from the aqueous phase. The filtered aqueous phase may contain a small amount of unreacted first phenolic compound, typically not greater than about 10 weight percent, more preferably about 1 to about 5 weight percent of the weight of the alkanesulfonic acid.

The weight-to-weight ratio of the water to the alkanesulfonic acid after quenching and combining of water washings depends, in part, on the extent of water washings required to render the chlorinated intermediate phase substantially free of the alkanesulfonic acid, but is preferably not less than about 1:4, more preferably not less than about 1:2, and most preferably not less than about 1:1; and preferably not greater than about 10:1, more preferably not greater than about 5:1, and most preferably not greater than about 3:1.

In a preferred mode of the process of the present invention, water is distilled or evaporated from the aqueous phase, preferably distilled at about 1 atmosphere or below, more preferably from about 50 to about 100 mm Hg absolute, to form a more highly concentrated alkanesulfonic acid. The weight-to-weight ratio of the water to the alkanesulfonic acid may become critically low during the course of the water removal, and measurable amounts of the alkanesulfonic acid may undesirably distill off along with the water. Such undesirable removal of acid can be virtually eliminated by the addition of an azeotropic excess of a second phenolic compound, that is, a sufficient amount of a second phenolic compound to the solution containing the water and alkanesulfonic acid to form a mixture which, when boiled or evaporated, results in the removal of substantially all of the water from the aqueous phase, but in the retention of substantially all of the alkanesulfonic acid and a portion of the added phenolic compound. The phenolic compound is selected to form an azeotrope with water, but not with the alkanesulfonic acid. Preferably, the second phenolic compound is the same as the phenolic compound used in the condensation reaction, more preferably phenol.

As used herein, the term "substantial absence of water" means not more than about 4, preferably not more than about 2, more preferably not more than about 1, and most preferably not more than about 0.5 weight percent, based on the weight of the alkanesulfonic acid, is present in the remnant after distillation. Likewise, the term "substantial absence of the alkanesulfonic acid" is used herein to refer to a distillate that contains not more than about 4, preferably not more than about 2, more preferably not more than about 1, and most preferably not more than about 0.5 weight percent, based on the weight of the water. Correspondingly, retaining "substantially all of the alkanesulfonic acid" means that not more than about 4, preferably not more than about 2, more preferably not more than about 1, and most preferably not more than about 0.5 weight percent alkanesulfonic acid, based on the weight of the water, is present in the distillate.

The amount of the second phenolic compound added to the aqueous phase depends on the amount of water and alkanesulfonic acid present. In the case where the phenolic compound is phenol, from about a 91:9 to about a 95:5 weight-to-weight water to phenol mixture (the azeotropic mixture) distills off at a constant temperature. The actual ratio of water to phenol in the azeotropic mixture depends on the pressure at which distillation takes place. For example, at about 50 mm Hg absolute, the azeotropic mixture is about a 94:6 weight to weight ratio of water to phenol. Thus, the amount of phenol added to the aqueous phase to ensure that some phenol is left in the phase after substantial removal of water at about 50 mm Hg absolute is greater than about 6/94 of the amount of water present in the aqueous phase. This critical amount is referred to as "an azeotropic excess".

More preferably, the amount of the second phenolic compound that is added to the aqueous phase is sufficient to ensure that the amount of the second phenolic compound that remains after substantial removal of the water is about equal to the amount of the second phenolic compound that is used in a condensation reaction of a phenolic compound and an α-haloketone to form a halogenated intermediate of a dihydroxy-α-alkylstilbene.

More particularly, the mole-to-mole ratio of the second phenolic compound to the alkanesulfonic acid prior to azeotropic removal of water is preferably not less than about 0.1:1, more preferably not less than about 0.5:1, and most preferably not less than about 1:1; and preferably not more than about 10:1, more preferably not more than about 5:1, and most preferably not more than about 3:1.

The second phenolic compound is preferably added to the aqueous phase at an alkanesulfonic acid concentration of not greater than about 90, more preferably not greater than about 80 weight percent; and preferably not less than about 60 and more preferably not less than about 70 weight percent, based on the weight of the alkanesulfonic acid and water. After the second phenolic compound is added to the aqueous phase, the distillation pressure is preferably from about 10, more preferably from about 20, to about 100, more preferably to about 50 mm Hg absolute. The temperature at which distillation is carried out depends on the pressure, but is preferably not less than about 100° C., more preferably not less than about 120° C., and most preferably not less than about 140° C.; and preferably not more than about 190° C., more preferably not more than about 180° C., and most preferably not more than about 160° C.

Boiling or evaporation can be carried out by any suitable technique such as simple distillation or falling film evaporation. Falling film evaporation is preferred. The substantially water-free remnant that contains the alkanesulfonic acid and phenolic compound can be conveniently be recycled to prepare a dihydroxyα-alkylstilbene, more preferably DHAMS. The alkanesulfonic acid has been found to be preferably at least about 90 percent recoverable, resulting in a substantial raw material cost savings.

The foregoing description relates specifically to the addition of a second phenolic compound to an aqueous phase resulting from the alkanesulfonic acid catalyzed condensation reaction of a first phenolic compound with an α-haloketone, followed by azeotropic distillation. Nevertheless, it is to be understood that any water-containing alkanesulfonic acid may be rendered substantially water-free by addition of an azeotropic excess of a phenolic compound that forms an azeotrope with water but not with the alkanesulfonic acid, followed by azeotropic distillation of water and the phenolic compound.

The following example is for illustrative purposes only and is not intended to limit the scope of this invention.

EXAMPLE 1

Recycle of MSA from a Chlorinated DHAMS Intermediate

Into a jacketed flask fitted with a nitrogen inlet and outlet, an addition funnel, a thermometer, and an overhead stirrer is added methanesulfonic acid (192.2 g, 2 mol), phenol (107.55 g, 1.14 mol), and methylene chloride (10 g). The flask is cooled to less than −15° C. whereupon chloroacetone (27.83 g, 0.2857 mol) is added dropwise along with 2 mL of methylene chloride rinses. The temperature is adjusted to −10° C. to −12° C., and stirring is continued until gas chromatographic analysis of an aliquot of the mixture shows the chloroacetone peak to be less than 1 percent by area of the chlorinated intermediate peak. The mixture is cooled to −15° C., whereupon 100 g of cold methylene chloride (−20° C.), then 283 g of chilled water (0° C. to 5° C.) are added to form a biphasic mixture. The mixture is agitated and the temperature of the solution is raised to 0° C. Agitation is ceased, and the lower (organic) layer is drained off and poured into a flask containing water (358.2 g) and isopropanol (716 g, 910 mL) maintained at 65° C. The upper (aqueous) layer is washed with an additional 50 mL of methylene chloride, which is drained off and added to the dechlorination reaction. The aqueous layer is heated under vacuum to remove residual methylene chloride and to convert any chloro-intermediate to trisphenol. The trisphenol is precipitated as a white powder, then filtered from the aqueous mixture. The aqueous acid is then distilled or sprayed or otherwise distributed onto the walls of a falling film evaporator to remove water as overhead stream. The still or evaporator is operated at less than 50 mm Hg absolute and the walls are heated to about 140° C. to produce acid of about 80 percent purity by weight. The phenol to be used in the next cycle is added to this stream along with sufficient phenol to remove the water as an azeotrope. The solution is then evaporated under vacuum, either by distillation or falling film evaporation to remove water as an azeotrope with phenol. Once water is removed to less than 0.5 percent, the acid and phenol are transferred back to the condensation reactor for the next reaction. The distillate containing the water and the phenol is used to quench and wash the subsequent dehydrochlorination reaction.

What is claimed is:

1. A process for removing water from an alkanesulfonic acid comprising the steps of:

a) condensing a first phenolic compound with an α-haloketone in the presence of an alkanesulfonic acid to form a hydrohalogenated intermediate of a dihydroxy-α-alkylstilbene;

b) quenching the condensation reaction with water to form a two-phase mixture, wherein one of the phases contains primarily water and the alkanesulfonic acid;

c) isolating the phase that contains primarily water and the alkanesulfonic acid, and adding thereto an azeotropic excess of a second phenolic compound to form a mixture of water, the alkanesulfonic acid, and the second phenolic compound; and d) boiling or evaporating off substantially all of the water and a portion of the second phenolic compound from the mixture of water, the alkanesulfonic acid, and the second phenolic compound to form a substantially water-free remnant that contains the alkanesulfonic acid and the second phenolic compound.

2. The process of claim 1 wherein the first phenolic compound is the same as the second phenolic compound.

3. The process of claim 2 wherein in step (c) the amount of the second phenolic compound that is added to the phase that contains primarily water and the alkanesulfonic acid is sufficient to ensure that the mole:mole ratio of the alkanesulfonic acid to the second phenolic compound in the substantially water-free remnant is not less than about 0.5:1 and not more than about 3:1.

4. The process of claim 3 wherein in step (c) water is removed from the phase that contains primarily water and the alkanesulfonic acid to form about a 70 to about a 90 weight percent solution of the alkanesulfonic acid, based on the weight of the alkanesulfonic acid and the water, prior to the addition of the second phenolic compound.

5. The process of claim 3 wherein the substantially water-free remnant contains not more than about 2 weight percent water, based on the weight of the alkanesulfonic acid in the remnant.

6. The process of claim 5 wherein the substantially water-free remnant contains not more than about 0.5 weight percent water, based on the weight of the alkanesulfonic acid in the remnant.

7. The process of claim 6 wherein the first and the second phenolic compounds are each phenol, the alkanesulfonic acid is methanesulfonic acid, and the α-haloketone is chloroacetone.

8. The process of claim 3 wherein the alkanesulfonic acid is methanesulfonic acid and the first and the second phenolic compounds are each phenol.

9. The process of claim 1 wherein in step (c) the amount of the second phenolic compound that is added to the phase that contains primarily water and the alkanesulfonic acid is sufficient to ensure that the mole:mole ratio of the alkanesulfonic acid to the second phenolic compound in the substantially water-free remnant is not less than about 0.1:1 and not more than about 10:1.

10. The process of claim 1 wherein the alkanesulfonic acid is methanesulfonic acid or ethanesulfonic acid.

11. The process of claim 1 wherein substantially all of the water is boiled or evaporated off using falling film evaporation.

* * * * *